United States Patent
Chan et al.

(10) Patent No.: US 11,013,543 B2
(45) Date of Patent: May 25, 2021

(54) METHOD OF PERFORMING A BALLOON KYPHOPLASTY PROCEDURE USING A SCOOP CANNULA

(71) Applicant: Medtronic Holding Company Sàrl, Tolochenaz (CH)

(72) Inventors: Hester Chan, Sunnyvale, CA (US); Amy L. Arthur, San Jose, CA (US); Trevor T. Seck, Saint Michael, MN (US)

(73) Assignee: MEDTRONIC HOLDING COMPANY SARL, Tolochenaz (CH)

( * ) Notice: Subject to any disclaimer, the term of this patent is extended or adjusted under 35 U.S.C. 154(b) by 186 days.

(21) Appl. No.: 15/988,544

(22) Filed: May 24, 2018

(65) Prior Publication Data

US 2019/0357955 A1    Nov. 28, 2019

(51) Int. Cl.
*A61B 17/88*    (2006.01)
*A61B 17/34*    (2006.01)

(52) U.S. Cl.
CPC ...... *A61B 17/8811* (2013.01); *A61B 17/3421* (2013.01); *A61B 17/3472* (2013.01); *A61B 17/8855* (2013.01); *A61B 2017/3454* (2013.01)

(58) Field of Classification Search
CPC ............ A61B 17/3421; A61B 17/7094; A61B 17/7097; A61B 17/8855; A61B 17/8819; A61B 17/8811; A61B 17/8858; A61B 17/1757; A61B 5/6853; A61B 17/8805
See application file for complete search history.

(56) References Cited

U.S. PATENT DOCUMENTS

| | | | |
|---|---|---|---|
| 4,239,042 A | 12/1980 | Asai | |
| 6,193,715 B1 | 2/2001 | Wrublewski et al. | |
| 8,454,620 B2 | 6/2013 | Ralph et al. | |
| 8,986,312 B2 | 3/2015 | Georgy | |

(Continued)

FOREIGN PATENT DOCUMENTS

| | | |
|---|---|---|
| EP | 3178426 A1 | 6/2017 |
| KR | 818384 B1 | 4/2008 |

(Continued)

OTHER PUBLICATIONS

Cook Medical, Bone Biopsy & Infusion Products, © Cook 2012 IR-BM-BBIP-EN-201201, www.cookmedical.com/edi.do, 24 pages.

*Primary Examiner* — Christopher J Beccia
(74) *Attorney, Agent, or Firm* — Sorell, Lenna & Schmidt, LLP

(57) ABSTRACT

A method of treating a bone of a patient includes identifying a portion of the patient to be protected. A cannula is provided that includes a shaft extending between opposite first and second end surfaces. The shaft includes an inner surface defining a lumen. The cannula includes a scoop extending from the second end surface. The scoop includes an inner surface that is continuous with the inner surface of the shaft and an opposite outer surface. The cannula is inserted into the bone such that the outer surface of the scoop is positioned adjacent to the portion of the patient to be protected. A balloon is inserted into the cannula such that the balloon is positioned within the scoop. The balloon is inflated such that the balloon expands away from the scoop as the balloon is inflated and creates a void in the bone. Systems are disclosed.

19 Claims, 7 Drawing Sheets

(56) References Cited

U.S. PATENT DOCUMENTS

| | | |
|---|---|---|
| 9,314,252 B2 | 4/2016 | Schaller et al. |
| 2005/0090852 A1* | 4/2005 | Layne .................. A61F 2/4601 606/190 |
| 2006/0264896 A1 | 11/2006 | Palmer |
| 2007/0293788 A1 | 12/2007 | Entrekin et al. |
| 2009/0198243 A1 | 8/2009 | Melsheimer |
| 2011/0202064 A1 | 8/2011 | O'Halloran et al. |
| 2013/0006257 A1 | 1/2013 | Lee |
| 2013/0013007 A1* | 1/2013 | Broome ............. A61B 17/8811 606/86 R |
| 2014/0235997 A1* | 8/2014 | Smith ................ A61B 17/8819 600/424 |
| 2017/0164978 A1* | 6/2017 | Dean ................. A61B 17/3472 |
| 2017/0231606 A1 | 8/2017 | White et al. |

FOREIGN PATENT DOCUMENTS

| | | |
|---|---|---|
| WO | 2011066465 A1 | 6/2011 |
| WO | 2014130521 A1 | 8/2014 |

\* cited by examiner

METHOD OF PERFORMING A BALLOON KYPHOPLASTY PROCEDURE USING A SCOOP CANNULA

TECHNICAL FIELD

The present disclosure generally relates to surgical methods, and more particularly to a method of treating bone using a scoop cannula in a kyphoplasty procedure. Systems are disclosed.

BACKGROUND

Height loss is commonly associated with spinal fractures, such as, for example, vertebral compression fractures. Spinal fractures affect a large segment of osteoporotic patients. It is estimated that approximately 700,000 spinal fractures occur annually from osteoporosis, for example. Procedures have been developed to treat spinal fractures. One such procedure is kyphoplasty. Kyphoplasty is a minimally invasive procedure that is used to treat spinal fractures, such as, for example, vertebral compression fractures by inserting one or more balloons, such as, for example, compliant balloons inside a fractured vertebral body. The balloon or balloons are inflated within the fractured vertebral body such that the cancellous bone of the vertebral body is pushed towards cortical walls of the vertebral body to form a cavity within the vertebral body. The cavity is then at least partially filled with a material, such as, for example, bone cement.

The balloons may be inserted into the vertebral body using a cannula, for example. Some cannulas include a scoop at the end of the cannula. The balloon engages the scoop to direct inflation of the balloon so that the balloon inflates away from the scoop. However, access to the vertebral body may be too inferior or superior, which creates the potential of breaking through an endplate and/or lateral wall of the vertebral body during the inflation process, which would prevent physicians from achieving the desired procedural outcome. This disclosure describes improvements over these prior art technologies.

SUMMARY

In one embodiment, a method of treating a bone of a patient includes identifying a portion of the patient to be protected. A cannula is provided that includes a shaft extending between opposite first and second end surfaces. The shaft includes an inner surface defining a lumen. The cannula includes a scoop extending from the second end surface. The scoop includes an inner surface that is continuous with the inner surface of the shaft and an opposite outer surface. The cannula is inserted into the bone such that the outer surface of the scoop is positioned adjacent to the portion of the patient to be protected. A balloon is inserted into the cannula such that the balloon is positioned within the scoop. The balloon is inflated such that the balloon expands away from the scoop as the balloon is inflated and creates a void in the bone. In some embodiments, system are disclosed.

In one embodiment, a method of treating a vertebra includes providing a cannula including a shaft extending between opposite first and second end surfaces. The shaft includes an inner surface defining a lumen. The cannula includes a scoop extending from the second end surface. The scoop includes an inner surface that is continuous with the inner surface of the shaft an opposite outer surface. A surgical pathway is created to the vertebra. The surgical pathway is positioned closer to a first endplate of the vertebra than a second endplate of the vertebra. The cannula is inserted through the surgical pathway and into the vertebra such that the outer surface of the scoop is positioned adjacent to the first endplate. A balloon is inserted into the cannula such that the balloon is positioned within the scoop. The balloon is inflated such that the balloon expands away from the scoop and the first endplate and towards the second endplate as the balloon is inflated to create a void in the vertebra while preventing the balloon from breaking through the first endplate. In some embodiments, the balloon is deflated and a bone filler material is delivered into the void. The bone filler material is allowed to cure within the void.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
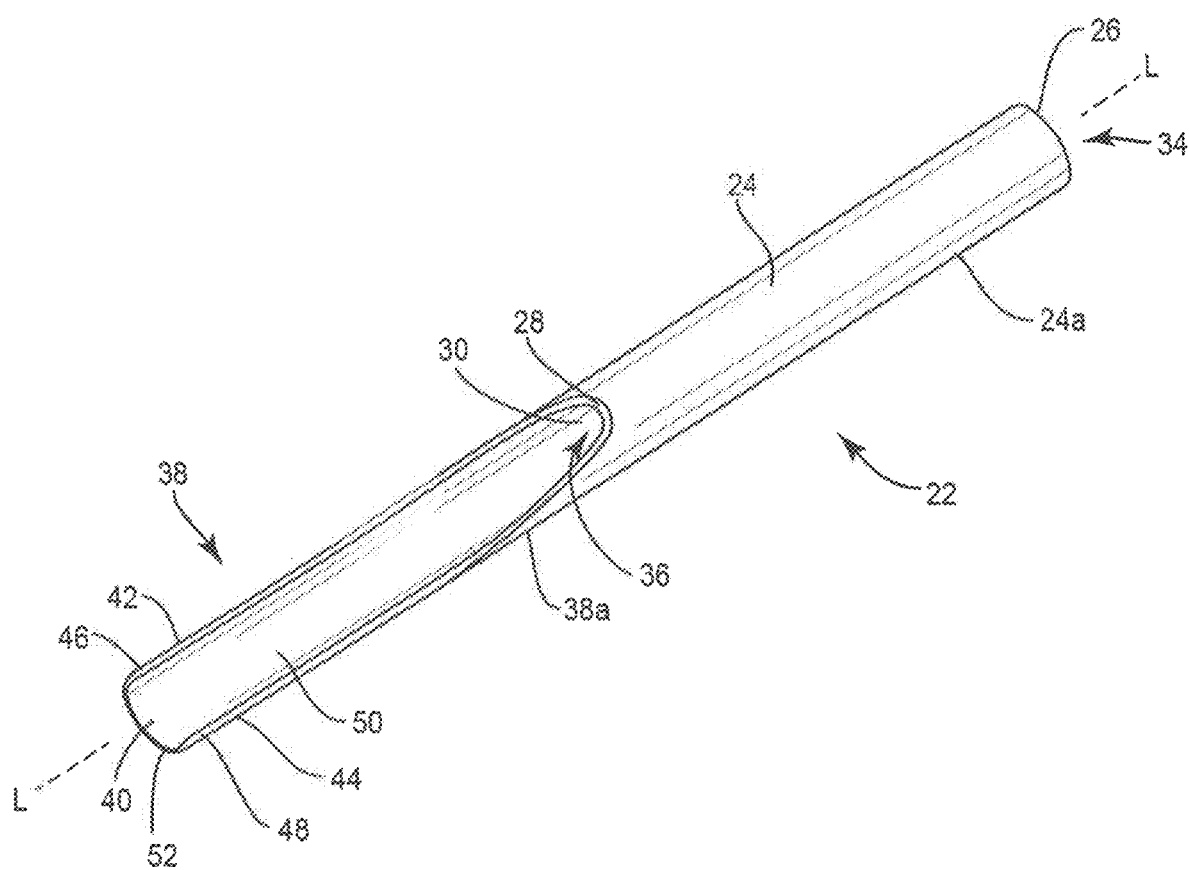
FIG. 1 is a perspective view of one embodiment of a component of a surgical system, in accordance with the present principles of the present disclosure.
Figure 2:
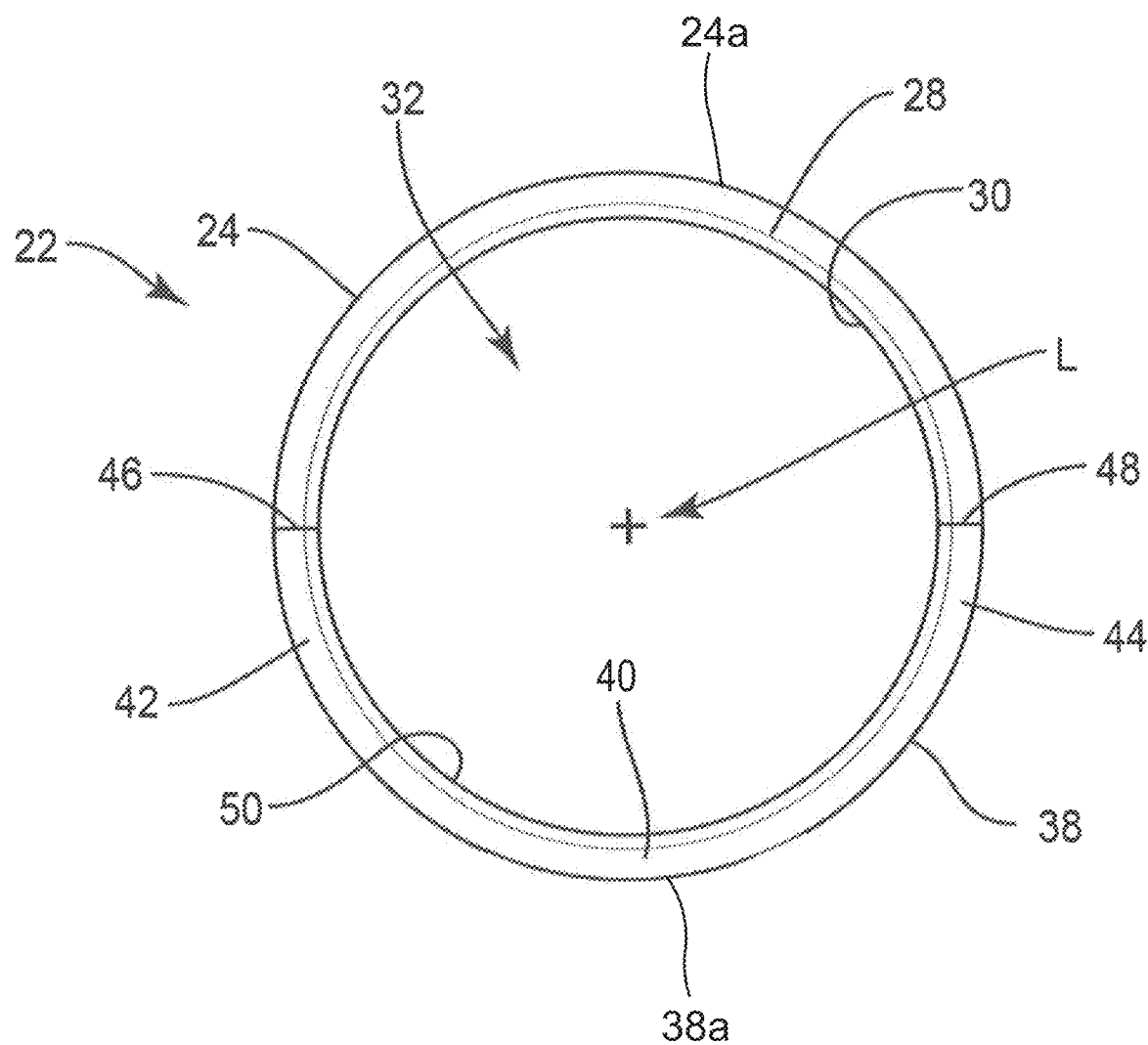
FIG. 2 is an end view of the component shown in FIG. 1.

The exemplary embodiments of a surgical method and related systems are discussed in terms of methods and systems for performing kyphoplasty. In some embodiments, the system includes a scoop cannula sized for the spine, such as, for example, size 2 and size 3 scoop cannulas. A scoop cannula is akin to a standard cannula found in existing osteo introducer system (OIS) tools, but has a cutout at the distal end. The cutout provides a platform for an inflatable bone tamp (IBT) to inflate against, thus allowing for unidirectional inflation of the IBT. The scoop cannula can be utilized in a "rescue" situation to assist physicians when the initial access with a standard OIS is less than ideal. If access with a standard OIS is too inferior or too superior, the IBT would have the potential of breaking through the endplate during the inflation process and the physicians would not be able to achieve the desired procedural outcome. The scoop cannula would be inserted down the same access channel with the platform oriented away from the closer endplate. As a result of the scoop cannula orientation, the inflation of the balloon would therefore be directed towards the further endplate, protecting the closer endplate from potential rupture. The scoop cannula could also be used in situations where the initial access was too lateral to help protect the lateral wall from rupturing during IBT inflation.

In some embodiments, one or all of the components of the surgical system may be disposable, peel-pack, pre-packed sterile devices. In some embodiments, the components of the surgical system are configured for one time use and are disposed after they are used one time. However, it is contemplated that one or all of the components of the surgical system may be reusable. The surgical system may be configured as a kit with multiple sized and configured components, including, for example, various scoop cannulas, balloons, etc. In some embodiments, one or more of the components of the surgical system are configured to be sterilized.

In some embodiments, the disclosed surgical methods and systems may be alternatively employed in a surgical treatment with a patient in a prone or supine position, and/or employ various surgical approaches, including anterior, posterior, posterior mid-line, direct lateral, postero-lateral, antero-lateral approaches, etc. in any body region. The methods and systems of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-7, there are illustrated components of a surgical system 20 in accordance with the principles of the present disclosure.

The components of surgical system 20 can be fabricated from biologically acceptable materials suitable for medical applications, including metals, synthetic polymers, ceramics and bone material and/or their composites, depending on the particular application and/or preference of a medical practitioner. For example, the components of surgical system 20, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of surgical system 20 may have material composites, including the above materials, to achieve various desired characteristics such as strength, rigidity, elasticity, compliance, biomechanical performance, durability and radiolucency or imaging preference. The components of surgical system 20, individually or collectively, may also be fabricated from a heterogeneous material such as a combination of two or more of the above-described materials. The components of surgical system 20 may be monolithically formed, integrally connected or include fastening elements and/or instruments, as described herein.

Surgical system 20 includes a scoop cannula, such as, for example, kyphoplasty cannula 22. Cannula 22 includes a shaft 24 that extends along a longitudinal axis L between a first end surface 26 and an opposite second end surface 28. Shaft 24 comprises an inner surface 30 defining a lumen 32. Lumen 32 is coaxial with axis L and extends the entire length of shaft 24. Lumen 32 has a circular cross-sectional configuration and a uniform diameter along the entire length of lumen 32. In some embodiments, lumen 32 may have various cross section configurations, such as, for example, oval, oblong, triangular, rectangular, square, polygonal, irregular, uniform, non-uniform, variable, tubular and/or tapered. In some embodiments, lumen 32 may be disposed at alternate orientations, relative to axis L, such as, for example, transverse and/or other angular orientations such as acute or obtuse, co-axial and/or may be offset or staggered. Shaft 24 comprises a first opening 34 that extends through end surface 26 and a second opening 36 that extends through end surface 28. Openings 34, 36 are each in communication with lumen 32.

Cannula 22 includes a semicircular plateau, such as, for example, a scoop 38 extending from end surface 28 along axis L such that scoop 38 faces away from end surface 26. Scoop 38 includes an outer surface 38a that is continuous with an outer surface 24a of shaft 24. That is, there are no gaps or recesses between outer surface 24a and outer surface 38a such that outer surface 24a smoothly transitions into outer surface 38a. In some embodiments, outer surface 38a extends parallel to outer surface 24a and/or axis L along an entire length of scoop 38. In some embodiments, outer surface 38a may be disposed at alternate orientations, relative to outer surface 24a and/or axis L, such as, for example, transverse, perpendicular and/or other angular orientations such as acute or obtuse, co-axial and/or may be offset or staggered.

Scoop 38 includes a center portion 40 that is positioned between side portions 42, 44 of scoop 38. Center portion 40 is configured to support a bottom surface of a balloon as the balloon is inflated such that the balloon expands away from scoop 38 and side portions 42, 44 are each configured to support a side surface of a balloon as the balloon is inflated to prevent the balloon from rolling over scoop 38 as the balloon is inflated, as discussed herein. In some embodiments, side portions 42, 44 are each tapered from end surface 28 to a distal end surface 52 of scoop 38. That is, side portions 42, 44 each have a height adjacent to end surface 28 that is greater than a height of side portions 42, 44 adjacent to distal end surface 52. In some embodiments, side portions 42, 44 are each continuously tapered from end surface 28 to a distal end surface 52 of scoop 38.

Side portion 42 includes a top surface 46 and side portion 44 includes a top surface 48. Scoop 38 includes an arcuate inner surface 50 that is continuous with inner surface 30 of shaft 24. That is, there are no gaps or recesses between inner surface 30 and arcuate inner surface 50 such that inner surface 30 smoothly transitions into arcuate inner surface 50. Arcuate inner surface 50 is configured to support a bottom surface of a balloon as the balloon is inflated to provide a backstop for the balloon to inflate against, as discussed herein. In some embodiments, arcuate inner surface 50 is concavely curved from top surface 46 to top surface 48. In some embodiments, arcuate inner surface 50 is continuously curved from top surface 46 to top surface 48. That is, arcuate inner surface 50 is even or smooth and free of any gaps or protrusions from top surface 46 to top surface 48 along the entire length of arcuate inner surface 50. In some embodiments, arcuate inner surface 50 has a continuous radius of curvature from top surface 46 to top surface 48. In some embodiments, arcuate inner surface 50 has a radius of curvature from top surface 46 to top surface 48 that is equal to the radius of curvature of inner surface 30 of shaft 24. In some embodiments, arcuate inner surface 50 has a radius of curvature from top surface 46 to top surface 48 that is greater than the radius of curvature of inner surface 30 of shaft 24. In some embodiments, arcuate inner surface 50 has a radius of curvature from top surface 46 to top surface 48 that is less than the radius of curvature of inner surface 30 of shaft 24.

In some embodiments, outer surface 38a of scoop 38 is convexly curved from top surface 46 to top surface 48. In some embodiments, outer surface 38a is continuously curved from top surface 46 to top surface 48. That is, outer surface 38a is even or smooth and free of any gaps or protrusions from top surface 46 to top surface 48 along the entire length of outer surface 38a. In some embodiments, outer surface 38a has a continuous radius of curvature from top surface 46 to top surface 48. In some embodiments, outer surface 38a has a radius of curvature from top surface 46 to top surface 48 that is equal to the radius of curvature of outer surface 24a of shaft 24. In some embodiments, outer surface 38a has a radius of curvature from top surface 46 to top surface 48 that is greater than the radius of curvature of outer surface 24a of shaft 24. In some embodiments, outer surface 38a has a radius of curvature from top surface 46 to top surface 48 that is less than the radius of curvature of outer surface 24a of shaft 24.

In some embodiments, shaft 24 and/or scoop 38 are made from a shape memory material. In some embodiments, shaft 24 and/or scoop 38 are made from a superelastic material. In some embodiments, shaft 24 and/or scoop 38 are made from super-elastic Nitinol. In some embodiments, shaft 24 and/or scoop 38 are made from a material that will deform elastically and then return to its original shape to minimize the effects of deformation. For example, shaft 24 and/or scoop 38 are made from super-elastic Nitinol such that side portions 42, 44 will deflect relative to center portion 40 when the balloon is inflated and then return to their original shape after the balloon is deflated. In some embodiments, shaft 24 and/or scoop 38 are made from a rigid material that cannot bend and/or deform without breaking. In some embodiments, shaft 24 is made from a rigid material that cannot bend and/or deform without breaking and scoop 38 is made from a shape memory material or a superelastic material. In some embodiments, scoop 38 is made from a rigid material that cannot bend and/or deform without breaking and shaft 24 is made from a shape memory material or a superelastic material.

Figure 3:
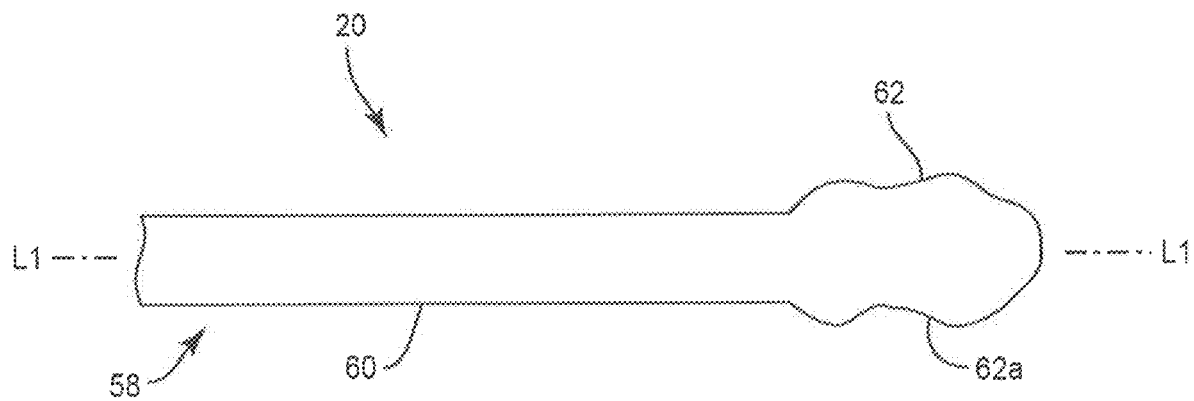
FIG. 3 is a side, cross sectional view of a component of the surgical system, in accordance with the present principles of the present disclosure.
Figure 4:
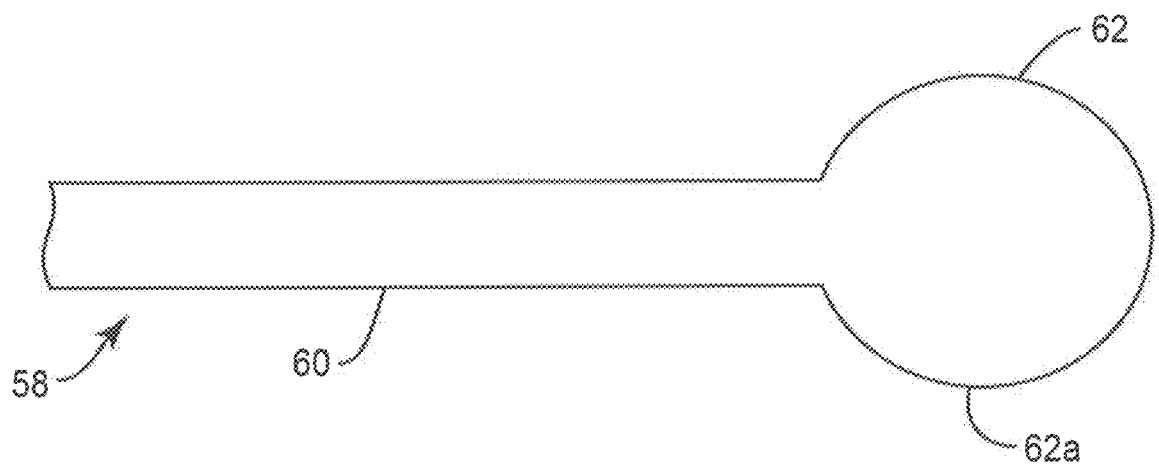
FIG. 4 is a side, cross sectional view of the component shown in FIG. 3.

System 20 includes a balloon catheter, such as, for example, an inflatable bone tamp 58. In one embodiment, shown in FIGS. 3 and 4, inflatable bone tamp 58 includes an outer tube, such as, for example, a tube 60 and a balloon 62 that is coupled to an end of tube 60. An inflation material, such as, for example, air, saline, or a contrast solution may be delivered through tube 60 and into balloon 62 to move balloon 62 from an uninflated orientation shown in FIG. 3 to an inflated orientation shown in FIG. 4. In some embodiments, balloon 62 is configured to expand radially about a longitudinal axis L1 defined by tube 60, as shown in FIGS. 3 and 4. In some embodiments, balloon 62 may configured to expand in only one direction. For example, balloon 62 may be made such that a top portion of balloon 62 is thicker or comprises a different material than a bottom portion of balloon 62 such that the bottom portion of balloon 62 will expand more than the top portion of balloon 62 when balloon 62 is inflated.

Figure 5:
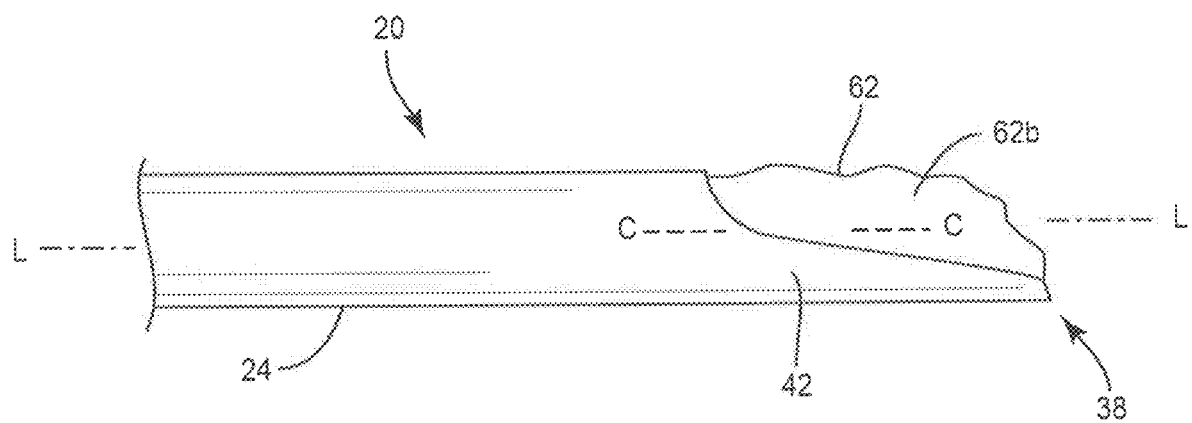
FIG. 5 is a plan view of the components shown in FIGS. 1 and 3.
Figure 6:
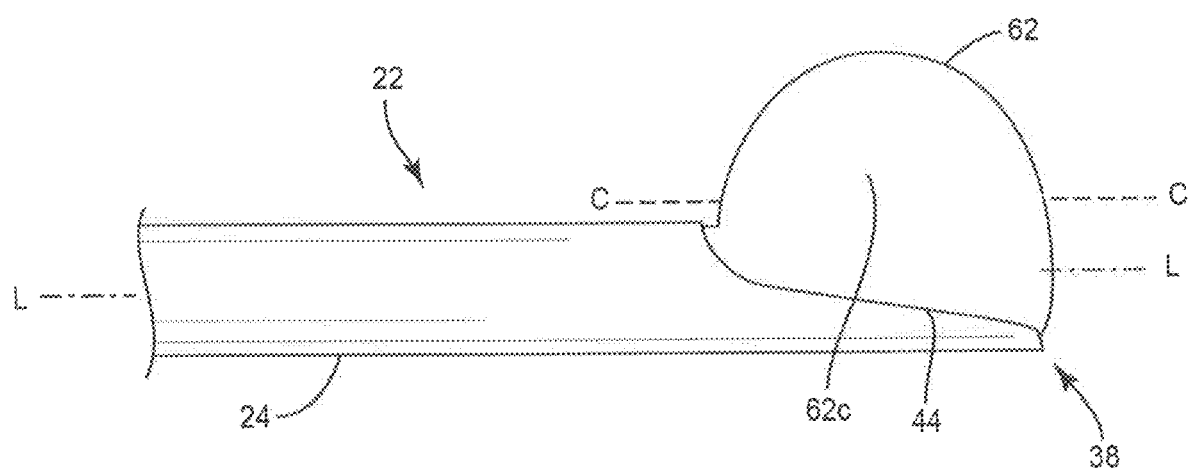
FIG. 6 is a plan view of the components shown in FIGS. 1 and 3.

Inflatable bone tamp 58 is configured for insertion into cannula 22 such that tube 60 is positioned within lumen 32 of shaft 24 and balloon 62 is positioned within scoop 38, as shown in FIGS. 5 and 6. In some embodiments, axis L is coaxial with axis L1 when inflatable bone tamp 58 is inserted into cannula 22. When balloon 62 is positioned within scoop 38, a bottom surface 62a of balloon 62 directly engages arcuate inner surface 50, a first side surface 62b of balloon 62 directly engages side portion 42 and an opposite second side surface 62c of balloon 62 directly engages side portion 44. As balloon 62 moves from the uninflated orientation to the inflated orientation, arcuate inner surface 50 supports bottom surface 62a of balloon 62 as balloon 62 is inflated to provide a backstop for balloon 62 to inflate against such that balloon 62 expands away from arcuate inner surface 50. Because balloon 62 expands away from scoop 38, a centerline C of balloon 62 is offset from axis L when balloon 62 is inflated, as shown in FIG. 6. In some embodiments, centerline C of balloon 62 may be coaxial with axis L when balloon 62 is uninflated, as shown in FIG. 5. Side portion 42 of scoop 38 supports side surface 62b of balloon 62 and side portion 44 of scoop 38 supports side surface 62c of balloon as balloon 62 moves from the uninflated orientation to the inflated orientation to prevent balloon 62 from rolling over scoop 38 as balloon 62 is inflated.

In operation and use, to treat a bone disorder, such as, for example, a spinal fracture, a medical practitioner obtains access to a target location including at least one bony structure, such as, for example, a fractured vertebra, in any appropriate manner, such as through incision and retraction of tissue. It is envisioned that the surgical system 20 may be used in any existing surgical method or technique including open surgery, mini-open surgery, minimally invasive surgery including percutaneous surgical implantation, whereby a vertebra of a patient is accessed through a micro-incision, or sleeve that provides a protected passageway to the area. Once access to the surgical site(s) are obtained, the particular surgical procedure is performed for treating the bone disorder.

A portion 64 of the patient is identified to be protected during inflation of balloon 62. In some embodiments, portion 64 is identified using computed tomography scan (CT), magnetic resonance image (MRI), CT capable fluoroscopy or similar two dimensional imaging study. In some embodiments, portion 64 is identified using radiography, via either a quantitative or semi-quantitative assessment. In some embodiments, a radiopaque contrast material is injected into the bone for visualization under radiographic imaging (fluoroscopy). In some embodiments, portion 64 is identified using an x-ray scan. In some embodiments, using either radiology or an x-ray scan, the image of a bone, such as, for example, a vertebra may be compared against other images to determine if the bone includes a fracture and/or other defect based on the shape of the bone and the shape of the bone(s) in the other images. In some embodiments, using either radiology or an x-ray scan, the image of a bone, such as, for example, a vertebra may be compared against mathematical models of normal bone to determine if the bone includes a fracture and/or other defect, using neighboring vertebrae as predictors of the unfractured shape of vertebrae. In some embodiments, portion 64 is identified using vertebral morphology techniques. In some embodiments, portion 64 is identified using a digital densitometry device that generates broadly based values of bone character, such as bone mineral content or bone mineral density. That is, portion 64 may be identified as a portion of bone having bone mineral content and/or bone mineral density below a selected threshold.

Figure 7:
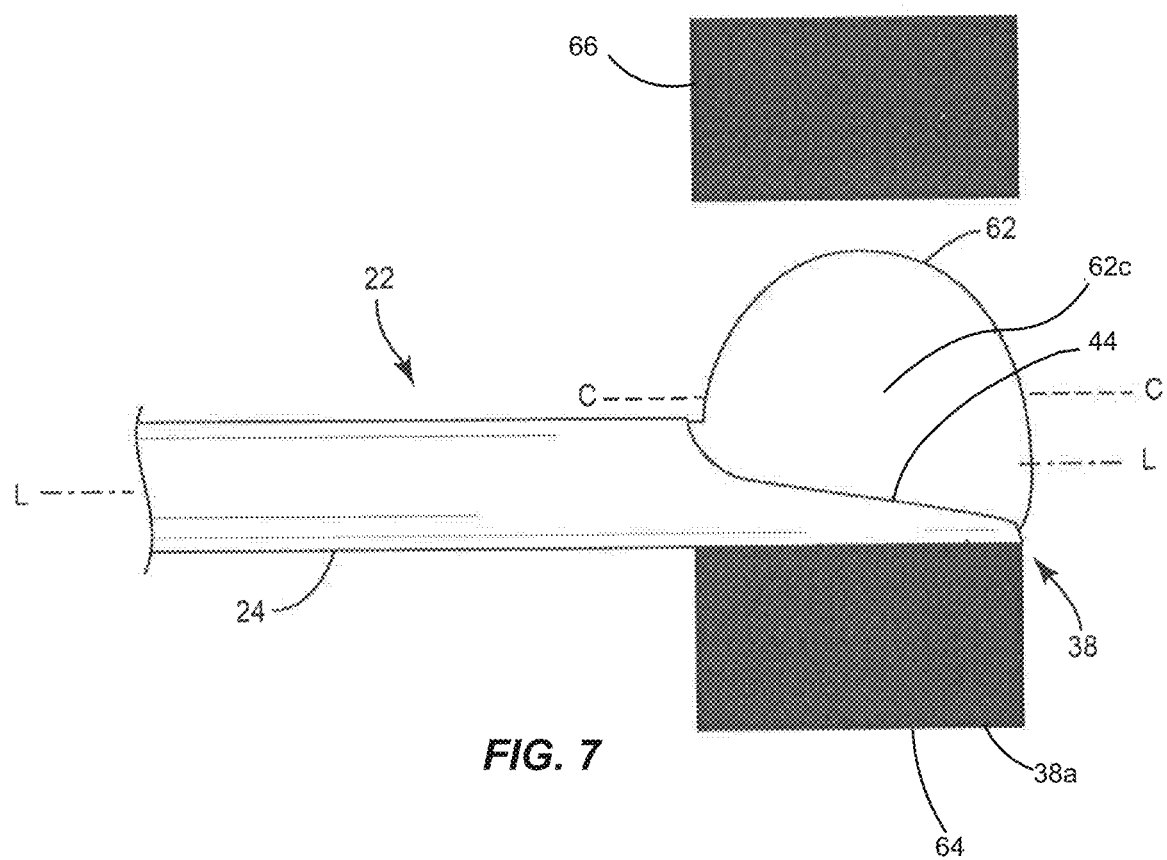
FIG. 7 is a plan view of the components shown in FIGS. 1 and 3.

In some embodiments, portion 64 is a nerve in or around a vertebra. In some embodiments, portion 64 is a bone fracture in or around a vertebra. In some embodiments, portion 64 is an endplate of a vertebra wherein the endplate includes a defect and/or is otherwise damaged. In some embodiments, portion 64 is a lateral wall of a vertebra. A surgical pathway is created to a bone, such as, for example, a vertebra. In some embodiments, the surgical pathway is positioned closer to a first endplate of the vertebra than a second endplate of the vertebra. In some embodiments, the surgical pathway is positioned closer to a first lateral wall of the vertebra than a second lateral wall of the vertebra. Inflatable bone tamp 58 is inserted into cannula 22 such that tube 60 is positioned within lumen 32 of shaft 24 and balloon 62 is positioned within scoop 38. Scoop 38 and balloon 62 are inserted through the surgical pathway and into a vertebral body of the vertebra such that scoop 38 is positioned adjacent to portion 64, as shown in FIG. 7. In some embodiments, inflatable bone tamp 58 is inserted into cannula 22 before cannula 22 is inserted into the vertebral body. In some embodiments, inflatable bone tamp 58 is inserted into cannula 22 after cannula 22 is inserted into the vertebral body.

In some embodiments, inflatable bone tamp 58 is inserted into cannula 22 such that balloon 62 is positioned entirely within scoop 38 such that balloon 62 will expand away from scoop 38 as balloon 62 is inflated. In some embodiments, a distal end of balloon 62 is recessed inwardly from a distal end of scoop 38. In some embodiments, the distal end of balloon 62 is flush with the distal end of scoop 38. In some embodiments, inflatable bone tamp 58 is inserted into cannula 22 such that the distal end of balloon 62 is distal to the distal end of scoop 38. In some embodiments, the distal end of balloon 62 laps over the distal end of scoop 38. In such embodiments, balloon 62 is a unidirectional balloon such that the portion of balloon 62 that is distal to the distal end of scoop 38 will expand away from portion 64. It is envisioned that balloon 62 may have walls with varying thickness, for example, to provide balloon 62 with unidirectional expansion capabilities.

In one embodiment wherein portion 64 is a nerve, cannula 22 may be positioned relative to the nerve such that outer surface 38a of scoop 38 faces the nerve and inner surface 50 of scoop 38 faces away from the nerve. In one embodiment wherein portion 64 is a nerve, cannula 22 may be positioned relative to the nerve such that outer surface 38a of scoop 38 directly engages the nerve. Balloon 62 is then moved from the uninflated orientation to the inflated orientation. As balloon 62 moves from the uninflated orientation to the inflated orientation, arcuate inner surface 50 of scoop 38 supports bottom surface 62a of balloon 62 as balloon 62 is inflated to provide a backstop for balloon 62 to inflate against such that balloon 62 expands away from the nerve. This allows a medical practitioner to direct balloon 62 away from the nerve. For example, scoop 38 may be used to direct balloon 62 away from portion 64 and toward a wall of an endplate 66 of the vertebra, as shown in FIG. 7. As discussed herein, scoop 38 helps to distribute the load created by balloon 62 against the vertebra to increase the lifting force of balloon 62. As balloon 62 moves from the uninflated orientation to the inflated orientation, balloon 62 creates a void space within the vertebra.

In one embodiment wherein portion 64 is a bone fracture, cannula 22 may be positioned relative to the bone fracture such that outer surface 38a of scoop 38 faces the bone fracture and inner surface 50 of scoop 38 faces away from the bone fracture. In one embodiment wherein portion 64 is a bone fracture, cannula 22 may be positioned relative to the bone fracture such that outer surface 38a of scoop 38 directly engages the bone fracture. In some embodiments, scoop 38 may be positioned such that scoop 38 extends across the bone fracture. In some embodiments, scoop 38 may be positioned such that axis L extends parallel to the bone fracture. In some embodiments, scoop 38 may be positioned such that axis L extends transverse to the bone fracture. Balloon 62 is then moved from the uninflated orientation to the inflated orientation. As balloon 62 moves from the uninflated orientation to the inflated orientation, arcuate inner surface 50 of scoop 38 supports bottom surface 62a of balloon 62 as balloon 62 is inflated to provide a backstop for balloon 62 to inflate against such that balloon 62 expands away from the bone fracture. This allows a medical practitioner to direct balloon 62 away from the bone fracture. For example, scoop 38 may be used to direct balloon 62 away from the bone fracture and toward endplate 66 of the vertebra, as shown in FIG. 7. As discussed herein, scoop 38 helps to distribute the load created by balloon 62 against the vertebra to increase the lifting force of balloon 62. As balloon 62 moves from the uninflated orientation to the inflated orientation, balloon 62 creates a void space within the vertebra.

In one embodiment wherein portion 64 is a first endplate of the vertebra, such as, for example, a damaged and/or weakened first endplate of the vertebra, cannula 22 may be positioned relative to the first endplate such that outer surface 38a of scoop 38 faces the first endplate and inner surface 50 of scoop 38 faces away from the first endplate. In one embodiment wherein portion 64 is a damaged and/or weakened first endplate of the vertebra, cannula 22 may be positioned relative to the first endplate such that outer surface 38a of scoop 38 directly engages the first endplate. For example, cannula 22 may be positioned such that outer surface 38a of scoop 38 directly engages a bony layer of the first endplate. In some embodiments, scoop 38 directly engages a ring apophysis of the vertebra when outer surface 38a of scoop 38 directly engages a bony layer of the first endplate. In some embodiments, cannula 22 may be positioned between a bony layer of the first endplate and a layer of hyaline cartilage of the vertebra. In some embodiments, scoop 38 may be positioned such that scoop 38 extends across the first endplate. Balloon 62 is then moved from the uninflated orientation to the inflated orientation. As balloon 62 moves from the uninflated orientation to the inflated orientation, arcuate inner surface 50 of scoop 38 supports bottom surface 62a of balloon 62 as balloon 62 is inflated to provide a backstop for balloon 62 to inflate against such that balloon 62 expands away from the first endplate. This allows a medical practitioner to direct balloon 62 away from the first endplate. For example, scoop 38 may be used to direct balloon 62 away from the first endplate and toward endplate 66 of the vertebra, as shown in FIG. 7. As discussed herein, scoop 38 helps to distribute the load created by balloon 62 against the vertebra to increase the lifting force of balloon 62. As balloon 62 moves from the uninflated orientation to the inflated orientation, balloon 62 creates a void space within the vertebra between endplate 64 and endplate 66.

In one embodiment wherein portion 64 is a first lateral wall of the vertebra, such as, for example, a damaged and/or weakened first lateral wall of the vertebra that is positioned between first and second endplates of the vertebra, cannula 22 may be positioned relative to the first lateral wall such that outer surface 38a of scoop 38 faces the first lateral wall and inner surface 50 of scoop 38 faces away from the first lateral wall. In one embodiment wherein portion 64 is a damaged and/or weakened first lateral wall of the vertebra that is positioned between first and second endplates of the vertebra, cannula 22 may be positioned relative to the first lateral wall such that outer surface 38a of scoop 38 directly engages the first lateral wall. In some embodiments, scoop 38 may be positioned such that scoop 38 extends across the first lateral wall. Balloon 62 is then moved from the uninflated orientation to the inflated orientation. As balloon 62 moves from the uninflated orientation to the inflated orientation, arcuate inner surface 50 of scoop 38 supports bottom surface 62a of balloon 62 as balloon 62 is inflated to provide a backstop for balloon 62 to inflate against such that balloon 62 expands away from the first lateral wall. This allows a medical practitioner to direct balloon 62 away from the first lateral wall. For example, scoop 38 may be used to direct balloon 62 away from the first lateral wall and toward a second lateral wall 66 of the vertebra, as shown in FIG. 7. As discussed herein, scoop 38 helps to distribute the load created by balloon 62 against the vertebra to increase the lifting force of balloon 62. As balloon 62 moves from the uninflated orientation to the inflated orientation, balloon 62 creates a void space within the vertebra between lateral wall 64 and lateral wall 66.

In one embodiment, balloon 62 is deflated and inflatable bone tamp 58 is removed from cannula 22 after balloon 62 creates the void space within the vertebra. A bone filler material is inserted through cannula 22 and into the void space within the vertebra. In one embodiment, balloon 62 is deflated and cannula 22 and inflatable bone tamp 58 are removed from the vertebra after balloon 62 creates the void space within the vertebra. A second cannula (not shown) is inserted into the vertebra such that an end of the second cannula is positioned within the void space. A bone filler material is delivered through the second cannula and into the void space to fill all or a portion of the void space. In some embodiments, the bone filler material is a curable bone filler material, such as, for example, a polymethylmethacrylate based bone cement. The bone cement then cures within the vertebra to treat the vertebra by reducing pain, stabilizing the vertebra and/or restoring the vertebra back to its normal height.

In some embodiments, a kit containing one or more components of surgical system 20 is provided. The kit may comprise components from any of the embodiments discussed herein. In some embodiments, the kit comprises one or more of the inflation materials discussed herein. In some embodiments, the kit comprises one or more bone filler materials, such as, for example, bone cements made from polymethylmethacrylate. In some embodiments, the kit comprises a plurality of cannulas, such as, for example, cannulas 22 having different lengths configured for use with different size patients. In some embodiments, the kit comprises a plurality of cannulas, such as, for example, cannulas 22 having scoops 38 with different widths and/or lengths configured for use with different size balloons.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A method of treating a patient, the method comprising:
identifying a portion of the patient to be protected, wherein the portion of the patient to be protected is nerve;
providing a cannula comprising a shaft extending between opposite first and second end surfaces, the shaft comprising an inner surface defining a lumen, the cannula comprising a scoop, the scoop comprising opposite proximal and distal end surfaces, the proximal end surface extending from the second end surface, the scoop being tapered from the proximal end surface to the distal end surface, the scoop comprising an inner surface that is continuous with the inner surface of the shaft and an opposite outer surface;
inserting the cannula into the patient such that the outer surface of the directly engages the portion of the patient to be protected;
inserting a balloon into the cannula such that the balloon is at least partially positioned within the scoop; and
inflating the balloon such that the balloon expands away from the scoop as the balloon is inflated and creates a void in the patient.

2. A method as recited in claim 1, further comprising:
deflating the balloon;
removing the balloon from the cannula;
delivering a bone filler material through the cannula and into the void; and
allowing the bone filler material to cure within the void.

3. A method as recited in claim 1, further comprising:
deflating the balloon;
removing the cannula from the patient;
inserting a second cannula into the patient such that an end of the second cannula is positioned within the void; and
delivering a bone filler material through the second cannula and into the void; and
allowing the bone filler material to cure within the void.

4. A method of treating a patient, the method comprising:
identifying a portion of the patient to be protected, wherein the portion of the patient to be protected is a nerve;
providing a cannula comprising a shaft extending between opposite first and second end surfaces, the shaft comprising an inner surface defining a lumen, the cannula comprising a scoop, the scoop comprising opposite proximal and distal end surfaces, the proximal end surface extending from the second end surface, the scoop being tapered from the proximal end surface to the distal end surface, the scoop comprising an inner surface that is continuous with the inner surface of the shaft and an opposite outer surface;
creating a surgical pathway to the nerve;
inserting the cannula through the surgical pathway such that the outer surface of the scoop directly engages the nerve;
inserting a balloon into the cannula such that the balloon is positioned within the scoop; and
inflating the balloon such that the balloon expands away from the scoop to create a void in the patient.

5. A method as recited in claim 1, wherein the scoop is continuously tapered from the proximal end surface to the distal end surface.

6. A method as recited in claim 1, wherein the scoop has a height adjacent to the proximal end surface that is greater a height of the scoop adjacent to the distal end surface.

7. A method as recited in claim 1, wherein the balloon extends beyond the distal end surface when the balloon is inflated.

8. A method as recited in claim 4, further comprising:
deflating the balloon;
removing the balloon from the cannula;
delivering a bone filler material through the cannula and into the void; and
allowing the bone filler material to cure within the void.

9. A method as recited in claim 4, further comprising:
deflating the balloon;
removing the cannula from the patient;
inserting a second cannula into the patient such that an end of the second cannula is positioned within the void; and
delivering a bone filler material through the second cannula and into the void; and
allowing the bone filler material to cure within the void.

10. A method as recited in claim 4, wherein the scoop is continuously tapered from the proximal end surface to the distal end surface.

11. A method as recited in claim 4, wherein the scoop has a height adjacent to the proximal end surface that is greater a height of the scoop adjacent to the distal end surface.

12. A method as recited in claim 4, wherein the balloon extends beyond the distal end surface when the balloon is inflated.

13. A method of treating a patient, the method comprising:
identifying a portion of the patient to be protected, wherein the portion of the patient to be protected is a nerve in a vertebra;
providing a cannula comprising a shaft extending between opposite first and second end surfaces, the shaft comprising an inner surface defining a lumen, the cannula comprising a scoop, the scoop comprising opposite proximal and distal end surfaces, the proximal end surface extending from the second end surface, the scoop being tapered from the proximal end surface to the distal end surface, the scoop comprising an inner surface that is continuous with the inner surface of the shaft and an opposite outer surface;
inserting the cannula into the patient such that the outer surface of the directly engages the portion of the patient to be protected;
inserting a balloon into the cannula such that the balloon is at least partially positioned within the scoop; and
inflating the balloon such that the balloon expands away from the scoop as the balloon is inflated and creates a void in the patient.

14. A method as recited in claim 13, further comprising:
deflating the balloon;
removing the balloon from the cannula;
delivering a bone filler material through the cannula and into the void; and
allowing the bone filler material to cure within the void.

15. A method as recited in claim 13, further comprising:
deflating the balloon;
removing the cannula from the patient;
inserting a second cannula into the patient such that an end of the second cannula is positioned within the void; and
delivering a bone filler material through the second cannula and into the void; and
allowing the bone filler material to cure within the void.

16. A method as recited in claim 13, further comprising creating a surgical pathway to the vertebra before inserting the cannula into the patient.

17. A method as recited in claim 13, wherein the scoop is continuously tapered from the proximal end surface to the distal end surface.

18. A method as recited in claim 13, wherein the scoop has a height adjacent to the proximal end surface that is greater a height of the scoop adjacent to the distal end surface.

19. A method as recited in claim 13, wherein the balloon extends beyond the distal end surface when the balloon is inflated.

* * * * *